United States Patent
Sullivan et al.

(10) Patent No.: US 10,342,705 B1
(45) Date of Patent: Jul. 9, 2019

(54) NOISE REDUCTION METHODS AND APPARATUSES FOR BREATHING APPARATUSES AND HELMETS

(71) Applicant: Oceanit Laboratories, Inc., Honolulu, HI (US)

(72) Inventors: Christopher Sullivan, Honolulu, HI (US); Daniel Kokubun, Waipahu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 798 days.

(21) Appl. No.: 14/304,579

(22) Filed: Jun. 13, 2014

Related U.S. Application Data

(60) Provisional application No. 61/834,679, filed on Jun. 13, 2013.

(51) Int. Cl.

| | |
|---|---|
| *A62B 7/00* | (2006.01) |
| *A61F 11/14* | (2006.01) |
| *B63C 11/22* | (2006.01) |
| *A62B 7/10* | (2006.01) |
| *A62B 17/04* | (2006.01) |
| *A62B 17/00* | (2006.01) |
| *A62B 7/14* | (2006.01) |
| *A61F 9/06* | (2006.01) |

(52) U.S. Cl.
CPC ............ *A61F 11/14* (2013.01); *A61F 9/068* (2013.01); *A62B 7/10* (2013.01); *A62B 7/14* (2013.01); *A62B 17/003* (2013.01); *A62B 17/04* (2013.01); *B63C 11/2227* (2013.01)

(58) Field of Classification Search
CPC ....... A61M 2205/42; B63C 2011/2218; B63C 11/2209; B63C 11/2227; B63C 11/2236; A42B 3/166; A61F 11/14; A61F 9/06; A62B 7/00; A62B 7/10; A62B 9/02; A62B 9/022; A62B 9/027; A62B 17/00; A62B 17/003; A62B 17/008; A62B 17/04; A62B 99/00
USPC ............................................................ 2/423
See application file for complete search history.

(56) References Cited

U.S. PATENT DOCUMENTS

| | | | | |
|---|---|---|---|---|
| 2,805,419 A | * | 9/1957 | Finken .................... | A42B 3/166 2/416 |
| 3,680,556 A | * | 8/1972 | Morgan .................. | B63C 11/06 128/201.15 |
| 3,845,768 A | * | 11/1974 | Garrahan ................ | B63C 11/14 128/201.27 |
| 4,114,197 A | * | 9/1978 | Morton .................. | A42B 3/127 2/423 |

(Continued)

OTHER PUBLICATIONS

Anthony et al., "Review of Diver Noise Exposure", QinetiQ Research Report RR735, 2009.

*Primary Examiner* — Jan Christopher L Merene
*Assistant Examiner* — Joseph D. Boecker
(74) *Attorney, Agent, or Firm* — James Creighton Wray; Meera P. Narasimhan

(57) ABSTRACT

Noise reduction in face masks and helmets reduces ear damage and improves communication by reducing noise in demand regulators with air diffuser perforated plates, screens or open cell foam and by providing muffling chambers. Insertable earmuffs are slid into voids formed in interior padding. Oral-nasal masks are isolated from helmet padding. Various layered helmets shells and padding reduce internal noise.

21 Claims, 14 Drawing Sheets

(56) References Cited

U.S. PATENT DOCUMENTS

| | | | | |
|---|---|---|---|---|
| 4,219,017 | A * | 8/1980 | Shamlian | B63C 11/2209 128/204.26 |
| 4,436,090 | A * | 3/1984 | Darling | A61M 16/20 128/204.26 |
| 5,090,061 | A * | 2/1992 | Kamata | A42B 3/16 2/423 |
| 5,184,609 | A * | 2/1993 | Hart | B63C 11/2209 128/204.26 |
| 5,603,117 | A * | 2/1997 | Hudner, Jr. | A42B 3/127 2/423 |
| 5,632,048 | A * | 5/1997 | Mortell | A42B 3/166 2/423 |
| 6,029,282 | A * | 2/2000 | Buschman | A42B 3/163 128/866 |
| 6,154,890 | A * | 12/2000 | Deopuria | A42B 3/16 181/129 |
| 6,206,000 | B1 * | 3/2001 | Folsom | B63C 11/06 128/200.29 |
| 7,798,142 | B2 * | 9/2010 | Morgan | B63C 11/16 128/201.27 |
| 2002/0179154 | A1 * | 12/2002 | Taylor | B63C 11/2209 137/541 |
| 2003/0079751 | A1 * | 5/2003 | Kwok | A61M 16/06 128/206.15 |
| 2004/0194829 | A1 * | 10/2004 | Zaiser | A61M 16/10 137/544 |
| 2005/0051382 | A1 * | 3/2005 | Borgmeier | F16L 55/02745 181/252 |
| 2006/0212998 | A1 * | 9/2006 | Gath | A42B 3/16 2/423 |
| 2008/0127976 | A1 * | 6/2008 | Acker | A61M 16/08 128/204.18 |
| 2010/0043797 | A1 * | 2/2010 | Deas | A62B 9/02 128/205.24 |
| 2012/0102629 | A1 * | 5/2012 | Lott | A42B 3/166 2/410 |
| 2012/0145155 | A1 * | 6/2012 | Peake | A61M 16/0816 128/205.12 |
| 2015/0216250 | A1 * | 8/2015 | Takeuchi | A62B 17/04 128/866 |

* cited by examiner

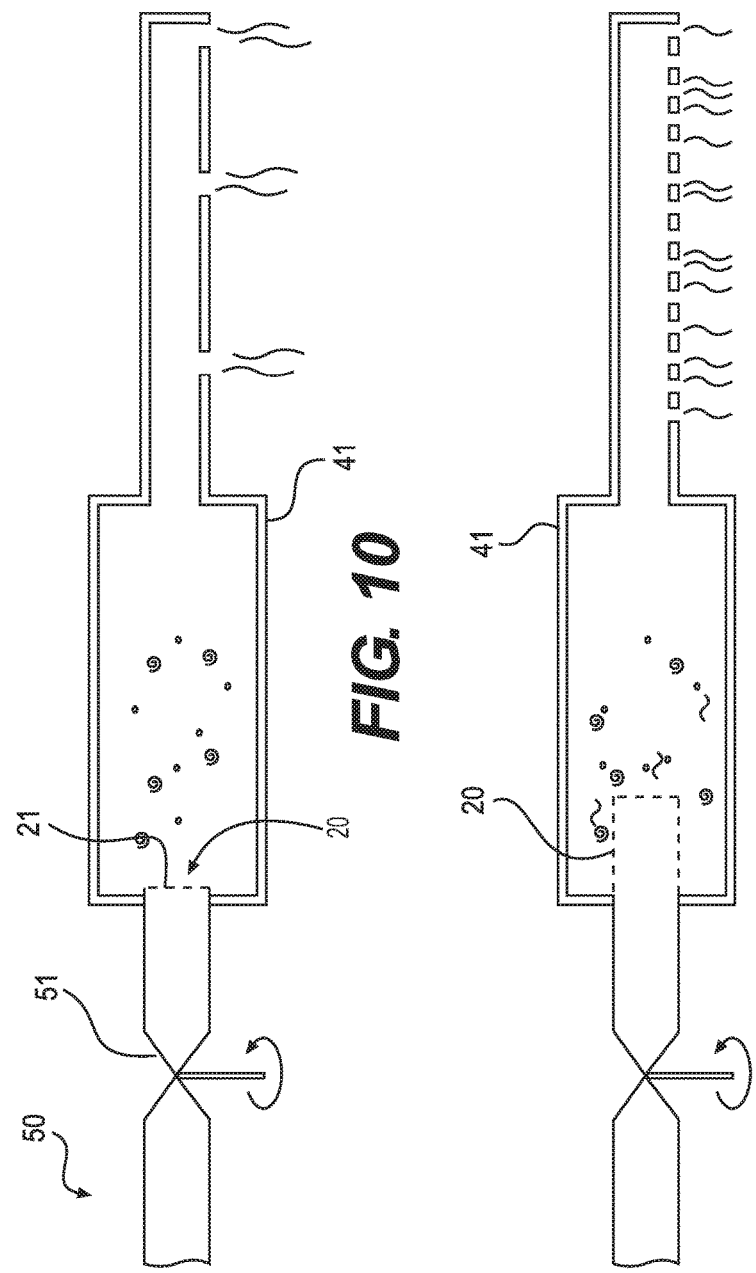

NOISE REDUCTION METHODS AND APPARATUSES FOR BREATHING APPARATUSES AND HELMETS

This application claims the benefit of U.S. Provisional Application No. 61/834,679 filed Jun. 13, 2014, which is hereby incorporated by reference in its entirety as if fully set forth herein.

This invention was made with Government support under Contract N00014-12-M-0362 awarded by the Office of Naval Research. The Government has certain rights in this invention.

BACKGROUND OF THE INVENTION

Divers can take on a wide range of tasks; underwater search and rescue, reconnaissance and salvage, demolition and construction, research or recreation. These tasks are complicated by the wide variety of conditions that they may be faced from shallow coastal tropical water and freshwater estuaries to deep ocean, arctic and ice covered ocean and timeframes that may be measured from minutes to days in the case of deep submergence and saturation diving as well as the desire to utilize communication systems.

Studies have shown that the difficulties of operating in these hazardous conditions are exacerbated by high levels of noise from a variety of sources both above and below the surface of sufficiently high intensity as to cause auditory damage. Typical sources in the divers' working environment might be blasts due to demolitions or repetitive noises due to underwater tools. In addition, self-generated noise such as airflow through a demand-regulator or the free flow air train can produce unacceptably noisy conditions. Divers are routinely exposed to a range of noise sources of sufficiently high intensity to cause auditory damage. Damage can be caused by high intensity short term exposure, but long-term exposure to levels exceeding 85 dB will cause hearing loss as well. Sources of damaging noise include:
- self-generated breathing/helmet noise
- ambient dive-site noise
- tool noise All of these sources depend on the environment and/or the diver responses. Even the self-generated breathing noise is impacted by the exertion level of the diver and can rise to damaging noise levels if physical activity and air demand are high. Acoustic levels of communications must exceed all background noise levels to be effective. Communications can actually produce more damage than other noise sources. Reducing other noise sources is critical to overall diver helmet sound levels. Some of these noise sources are common in self contained breathing apparatus (SCBA) and abrasive blasting hoods as well.

Needs exist for improved noise reduction and improved communication in helmets and SCBA and other breathing devices. Pilots and other helmet wearers would be benefited by improved noise reduction and communication in helmets.

SUMMARY OF THE INVENTION

The invention provides methods and apparatus for reducing noise in helmets, masks and SCBA, including those that use air supplies. Reducing noise sources allows communication levels to be reduced to safe levels. The invention reduces noise by reducing both self-generated and external noise via a series of modifications to dive helmets and respirator/regulators and components. New methods and apparatus include:

- modifying of secondary regulators (demand regulators) to reduce valve-generated noise without increasing diver breathing resistance levels, while improving communications,
- creating free-flow air train to reduce valve noise and other aerodynamically generated noise,
- isolating and dampening oral-nasal masks to reduce noise transmission to oral-nasal mask microphones and reduce mask vibrations,
- incorporating slide-in earmuffs in helmets to isolate helmet volume from ears,
- modifying helmet structure to reduce environmental transmission into helmet
- Identifying digital communications technology for integration into dive communications system The key features are:
- Modular upgrade-kit form factor allows application to existing helmets and SCBA's.
- Reduces breathing noise from secondary regulator (demand regulator) without increasing diver breathing resistance
- Reduces breathing noise picked up on communications systems
- Reduces noise from free-flow air train
- Reduces free-flow air train noise picked up on communications systems
- Incorporates slide-in modular earmuffs into modified modular hood/head cushion to isolate ears from helmet cavity
- Modular oral-nasal mask dampener/isolator reduces vibrations in the oral-nasal mask from talking and isolates microphone from the rest of the helmet, reducing noise on the communications system
- Reduces noise transmitted from externally generated noise sources over existing helmet shell designs using an alternative external shell design.

These and further and other objects and features of the invention are apparent in the disclosure, which includes the above and ongoing written specification, with the claims and the drawings.

BRIEF DESCRIPTION OF THE DRAWINGS

FIG. 10 shows a constant flow air train with an adjustment valve and a new orifice plate and silencing chamber.

FIG. 11 shows a constant flow air train with an adjustment valve and a new cylindrical air diffusing screen and a silencing muffler chamber.

DETAILED DESCRIPTION OF THE DRAWINGS

Figure 1:
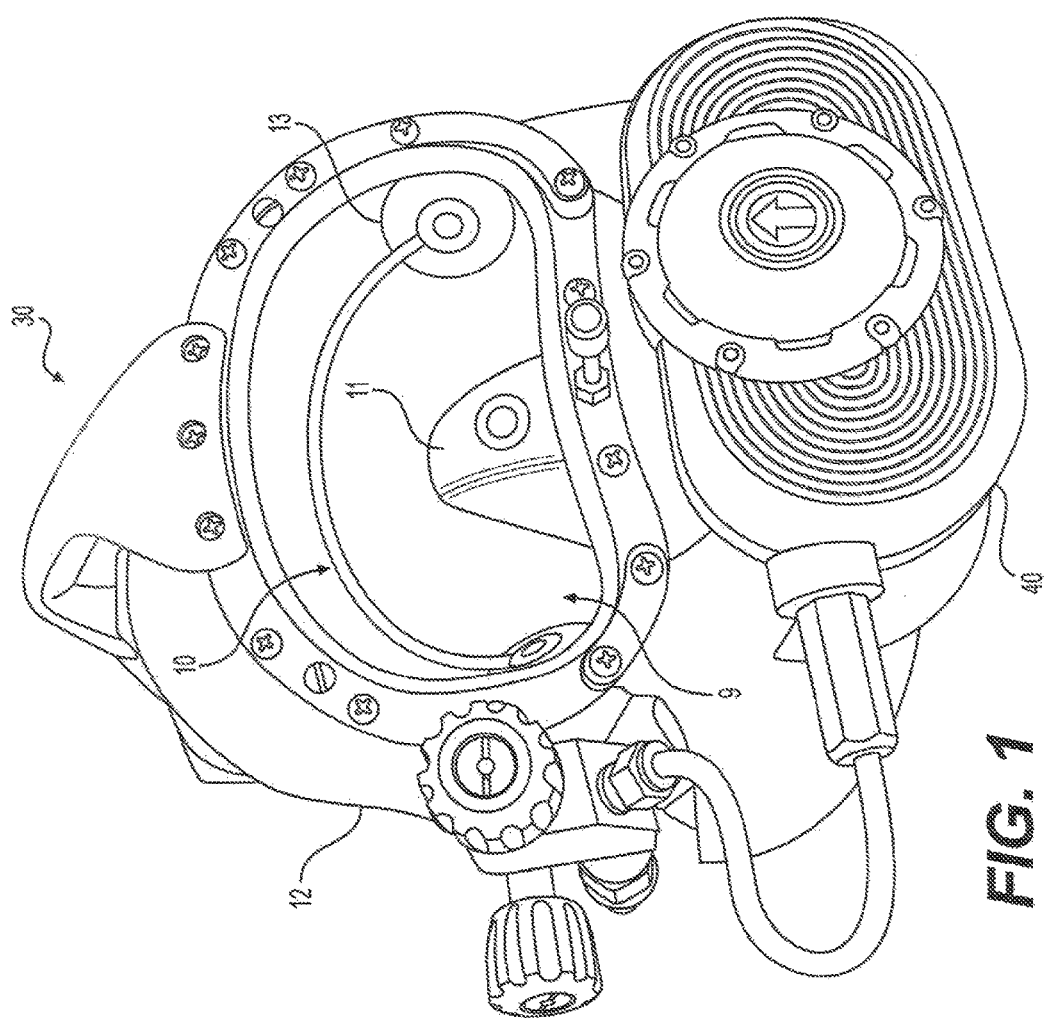
FIG. 1 is an illustration of a solution to dive helmet noise which addresses sources of noise as well as noise transmission paths.

FIG. 1 shows an example of a commercial dive helmet 30 improved with aspects of the current invention with a modified free-flow air train 10 above mask view port 9, alternative shell structure helmet construction 12, oral-nasal mask dampening jacket 11, integrated slide-in earmuffs 13, and a modified demand regulator 40. The redesigned free-flow air train 10 reduces free-flow noise. The new oral-nasal mask damping jacket 11 isolates the internal microphone from noise inside the helmet and reduces silicone mask speech vibration noise. The new alternative helmet shell design 12 can reduce external noise transmission. Integrated slide-in earmuffs 13 reduce required communication volume. Redesigned demand regulator 40 significantly reduces noise with no increase in breathing resistance.

Figure 2:
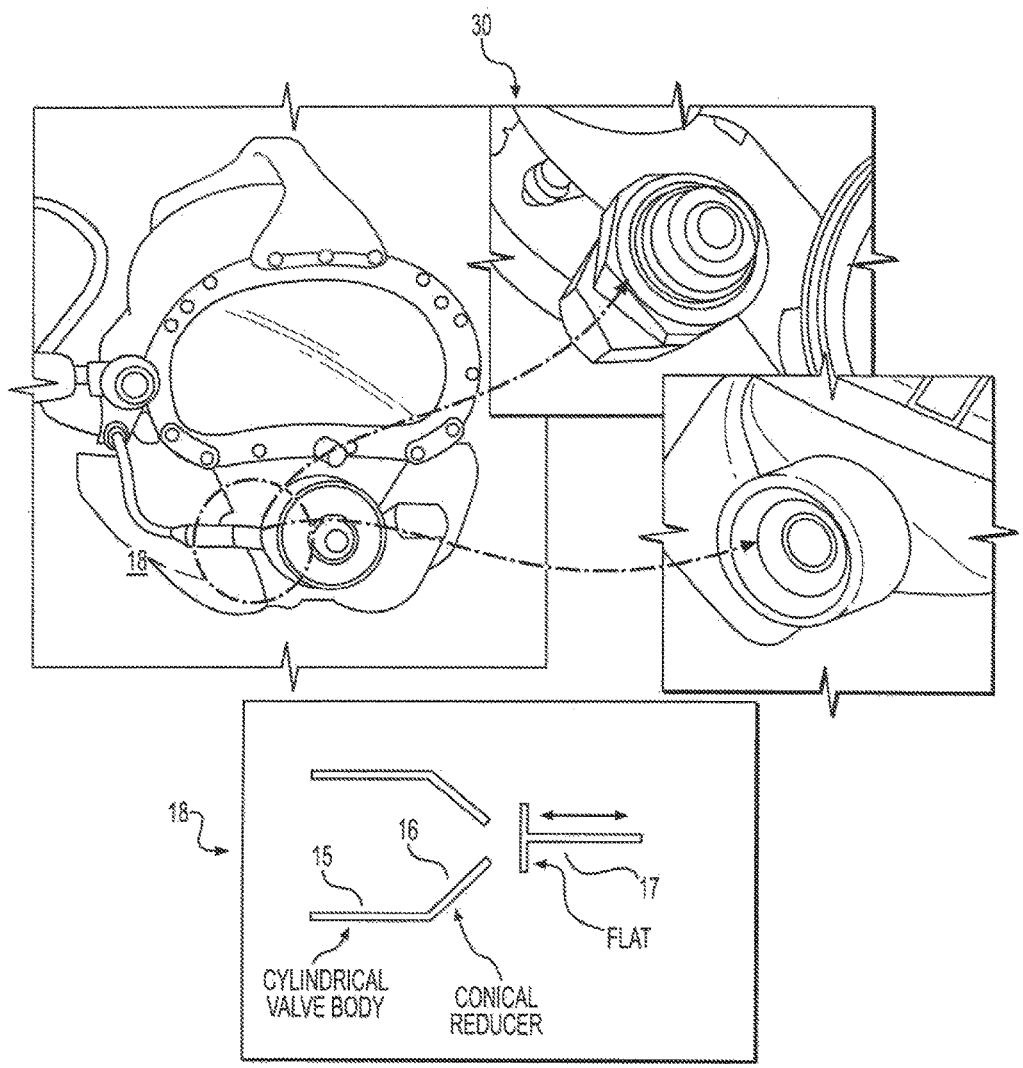
FIG. 2 shows the existing secondary regulator valve orifice located to the side of the main assembly.

FIG. 2 shows a prior art helmet 30 from FIG. 1 where a secondary regulator valve orifice body 15 is located to the side of the main helmet assembly 30. The demand regulator valve 18 on dive helmet 30 operates by opening this spring-loaded valve 17 using inhalation-induced pressure drop over a diaphragm. The valve 18 consists of cylindrical body 15 with a circular orifice on one end and a rubber-covered flat surface 17 on the other end. Air comes from a high-pressure source through the valve 18 into the lower pressure volume of the demand regulator 14 and into the helmet. As air moves from the high pressure to low pressure volumes in cylindrical body 15, the conical reducer 16 and through the orifice, sound is generated from turbulent air fluctuations at the valve opening, and the sounds propagate through the regulator housing and into the oral-nasal mask.

Figure 3:
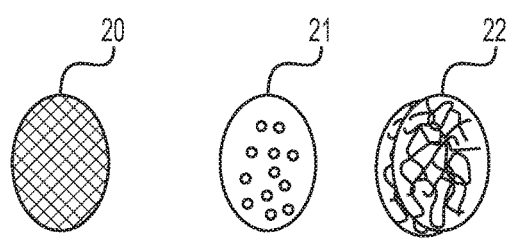
FIG. 3 shows noise reduction air diffusers as a screen, a perforated plate with small orifices and an open cell foam made of polymer, metal or other materials.

FIG. 3 shows various noise-reducing air flow diffusers and filters made of screen 20 porous sintered metal 21 and open cell foam 22 that are representative of small-pore flow restricting elements that are used in the current invention.

Figure 4:
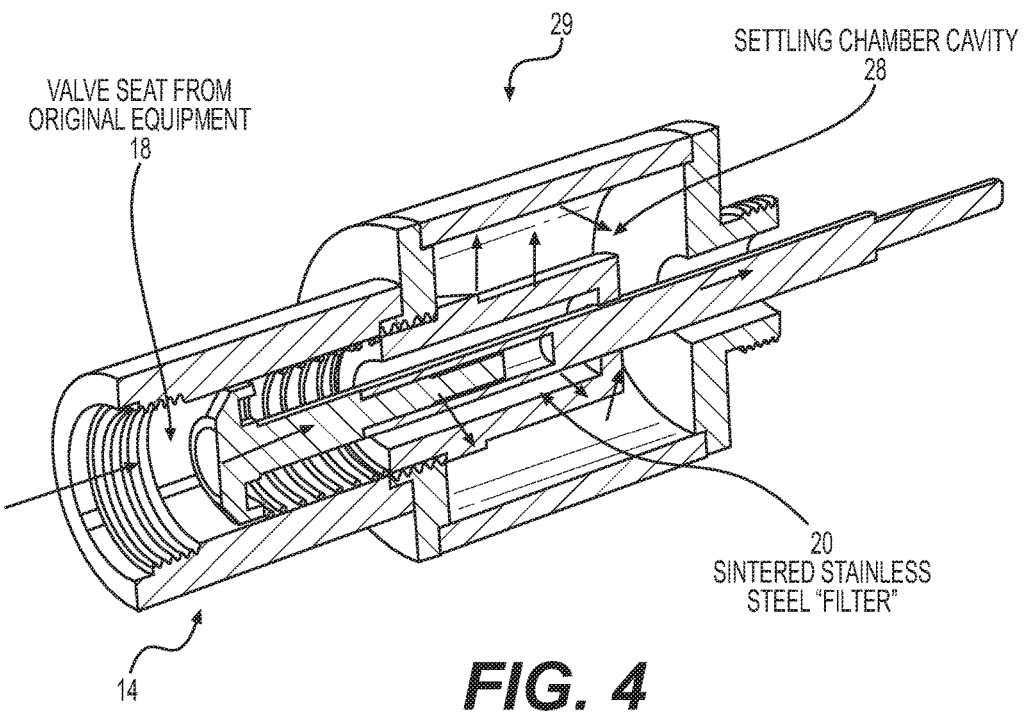
FIG. 4 is an example mechanism for silencing flow noise in a secondary regulator.

FIG. 4 shows an embodiment of the current invention that quiets noise in secondary regulators, for example. In this embodiment a sintered stainless steel filter element or other porous flow restricting mechanism and a settling chamber cavity 28 volume are incorporated into the valve body 14. The stock valve seat 18 is used, but air coming from the open valve is directed through a co-axial sintered metal or other porous flow restricting element 20 and into a settling chamber 28 before venting into the main housing.

Figure 5:
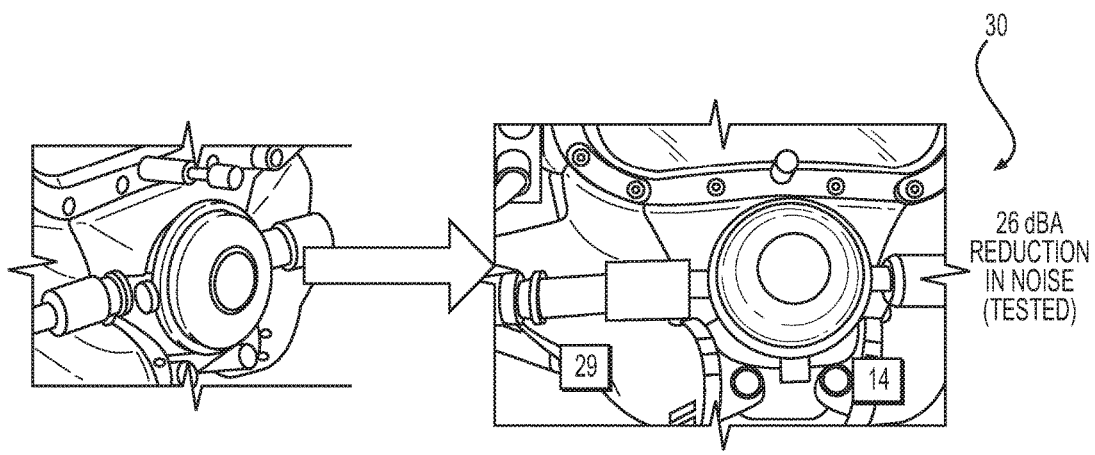
FIG. 5 is a comparison of the stock versus quiet modified design of demand regulator on a dive helmet.

FIG. 5 shows a stock picture of a demand regulator on the left alongside a picture on the right of the quiet modified demand regulator 29 containing the valve/silencer installed on an oral nasal mask 14 of a helmet 30.

Figure 6:
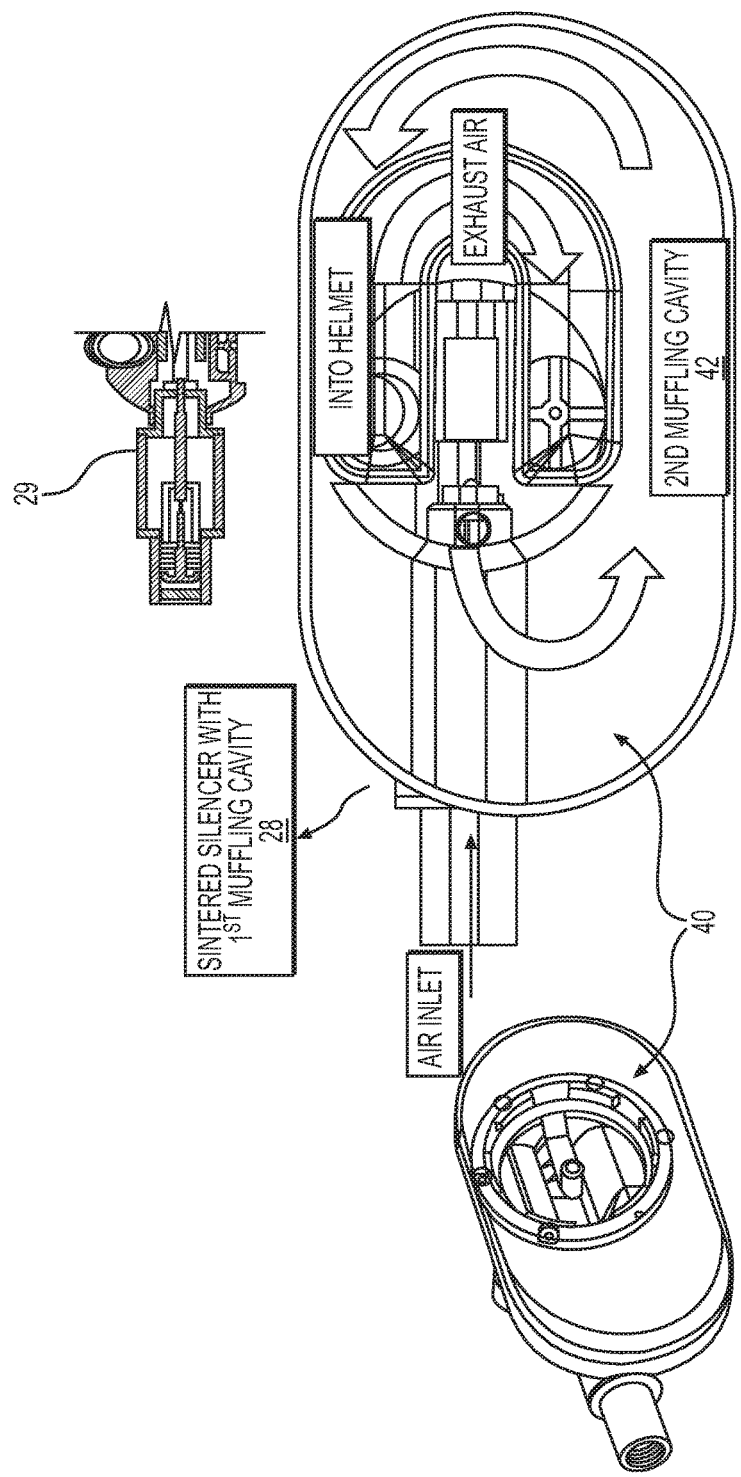
FIG. 6 shows an increased volume regulator assembly.

FIG. 6 shows a modified increased volume regulator assembly 40. Further reductions in noise from the secondary demand regulator were obtained by modifying and fabricating an integrated assembly with a larger volume regulator body 40. In this embodiment, the valve muffler assembly 29 is integrated into a modified demand regulator body 40. New regulator 40 has a sintered silencer in a first muffling cavity 28 and a second muffling cavity 42. The effect is that more sound transmission loss is achieved.

Figure 7:
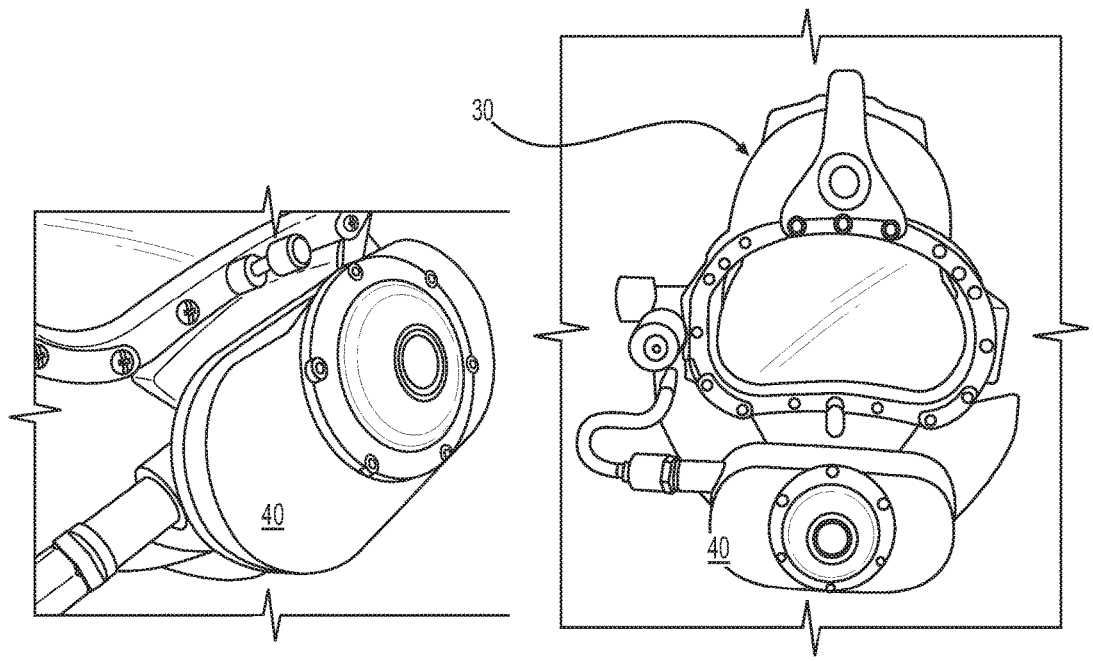
FIG. 7 shows an embodiment of the increased volume regulator integrated with a dive helmet.

FIG. 7 shows an example dive helmet 30 with an integrated manufactured increased volume regulator 40.

Figure 8:
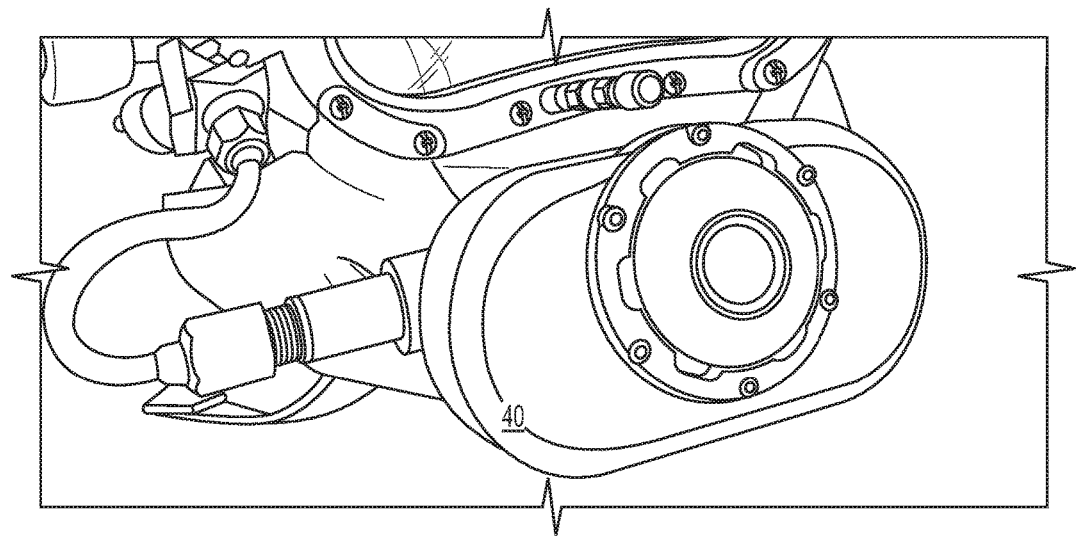
FIG. 8 shows the configuration of helmet and increased volume regulator fabricated in aluminum.

FIG. 8 shows the integrated regulator muffler body 40 fabricated in aluminum.

Figure 9:
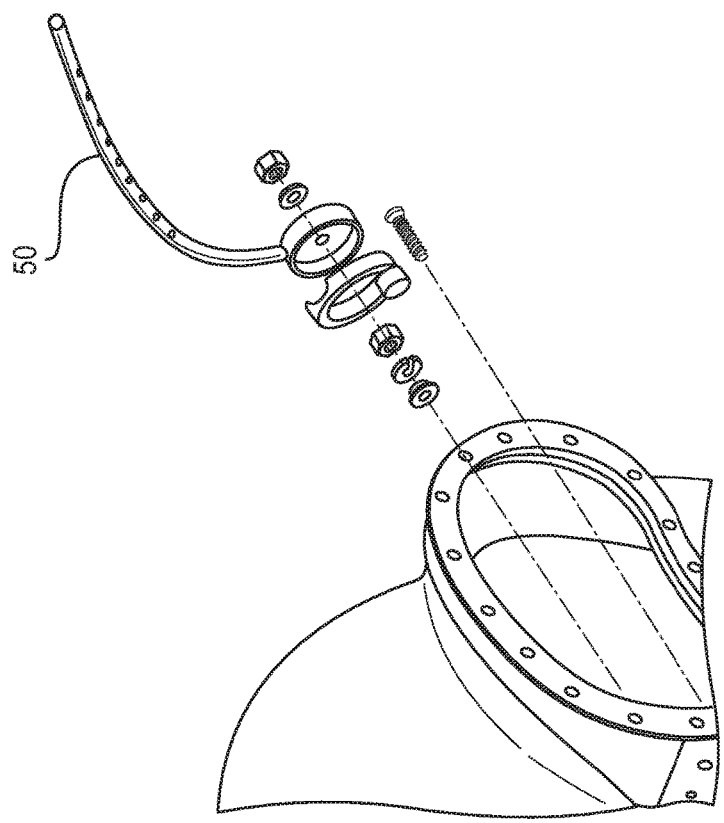
FIG. 9 shows a continuous flow air train connection to a helmet.

FIG. 9 shows a stock air train 50 connected to a dive helmet 30.

FIG. 10 shows a constant flow air train 50 with an adjustment valve 51 and a new orifice plate 21 and silencing chamber 41.

FIG. 11 shows a constant flow air train with an adjustment valve and a new cylindrical air diffusing screen 20 and a silencing muffler chamber 41.

Figure 12:
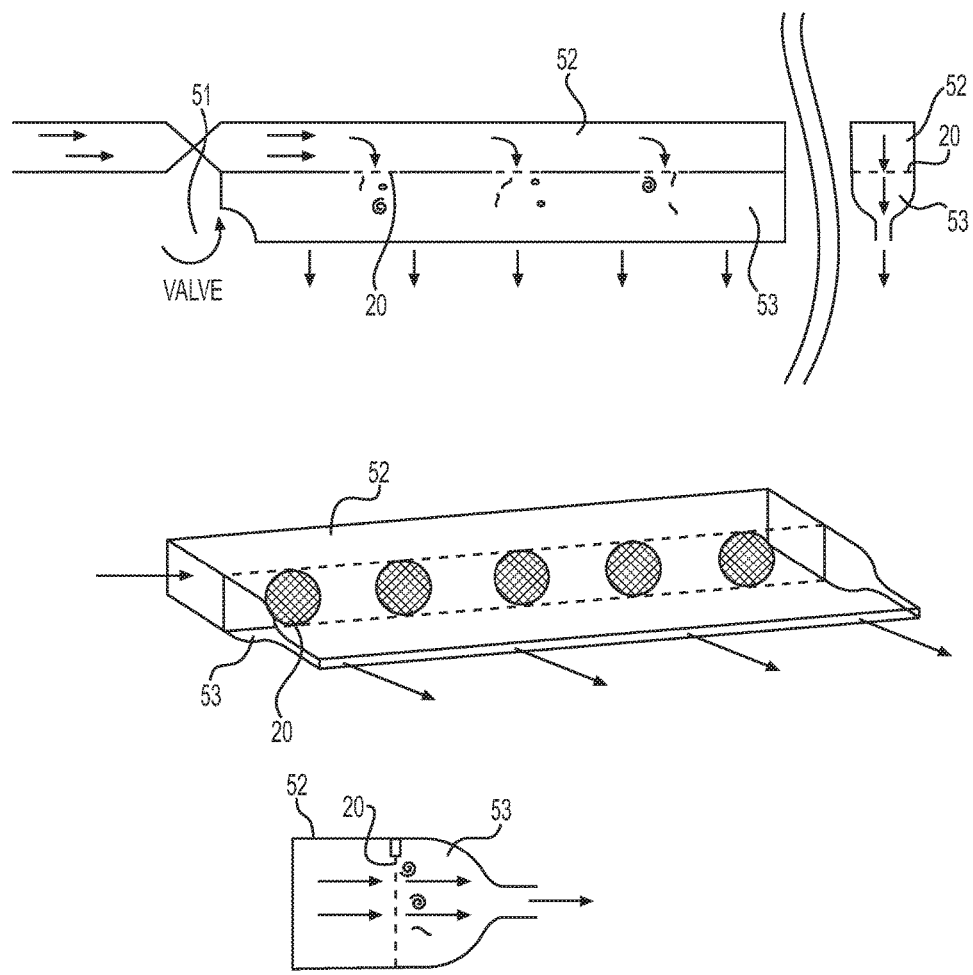
FIG. 12 shows continuous air flow through an adjustment valve, a distribution channel cavity, air diffusion screens and a silencing and concentrating chamber in cross-sectional side, perspective and end views.

FIG. 12 shows continuous air flow through an adjustment valve 51, a distribution channel cavity 52, air diffusion screens 20 and a silencing and concentrating chamber 53, in cross-sectional side, perspective and end views.

Figure 13:
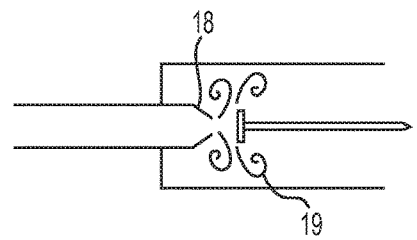
FIG. 13 shows a prior art air demand valve with noise causing eddies.

FIG. 13 shows a prior art air demand valve 18 with noise causing eddies 19.

Figure 14:
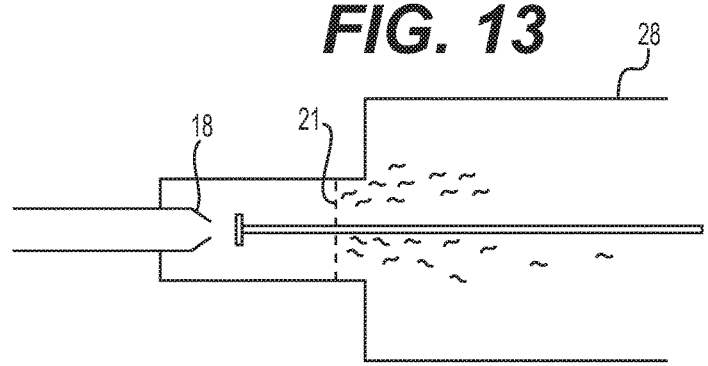
FIG. 14 shows a prior art air demand valve with an air diffusing plate and a muffling or silencing cavity.

FIG. 14 shows a prior art air demand valve 18 with a new air diffusing plate 21 and a muffling or silencing cavity 28.

Figure 15:
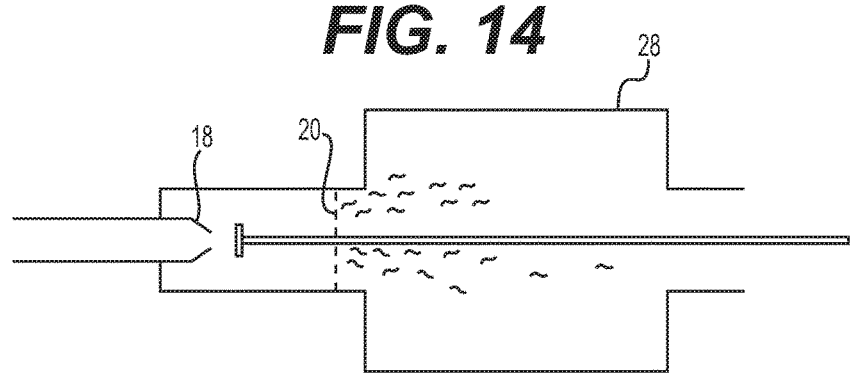
FIG. 15 shows a prior art air demand valve with an air diffusing screen and a muffling or silencing cavity.

FIG. 15 shows a prior art air demand valve 18 with a new air diffusing screen 20 and a muffling or silencing cavity 28.

Figure 16:
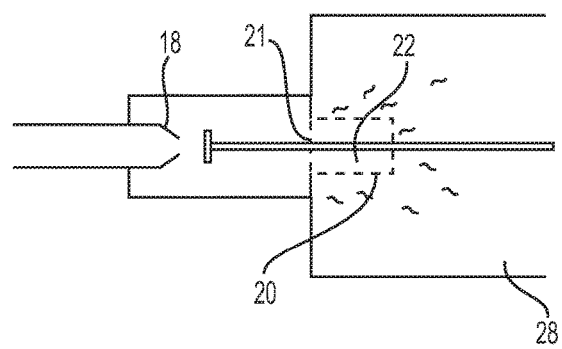
FIG. 16 shows a prior art air demand valve with an air diffusing cylindrical screen plate or open cell porous insert and a muffling or silencing cavity.

FIG. 16 shows a prior art air demand valve 18 with a new air diffusing cylindrical porous plate 21 with a cylindrical screen 20 which may contain or open cell porous insert 22 and a muffling or silencing cavity 28.

Figure 17:
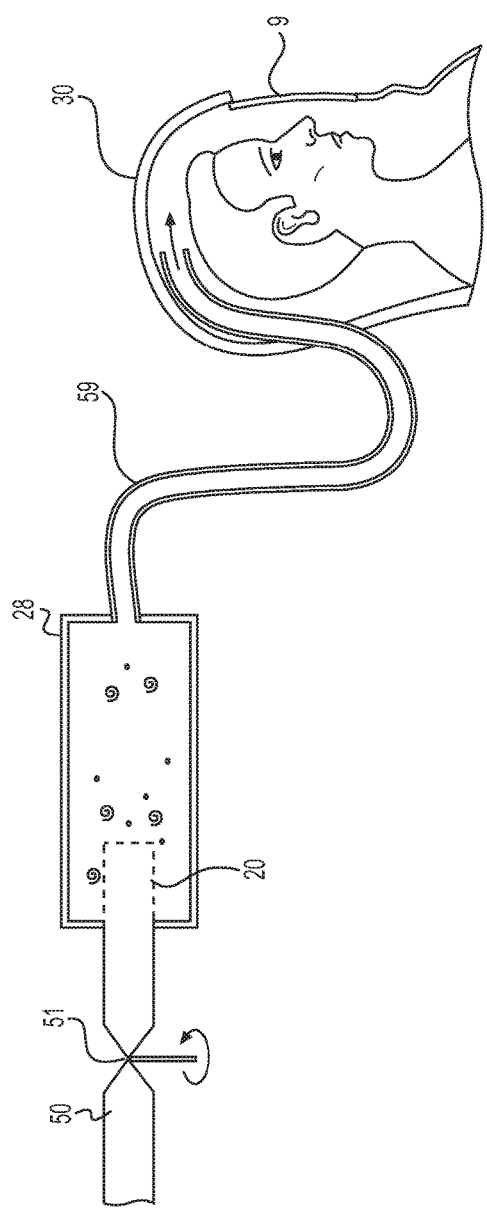
FIG. 17 shows a continuous air flow train through an adjustment valve, cylindrical screen plate or open cell porous insert and a silencing cavity and through a hose to the top of a helmet to direct air toward a view plate.

FIG. 17 shows a continuous air flow train 50 through an adjustment valve 51, cylindrical screen 20, plate or open cell porous insert and a silencing cavity 41 and through a hose 59 to the top of a helmet 30 to direct air toward a view plate 9.

Figure 18:
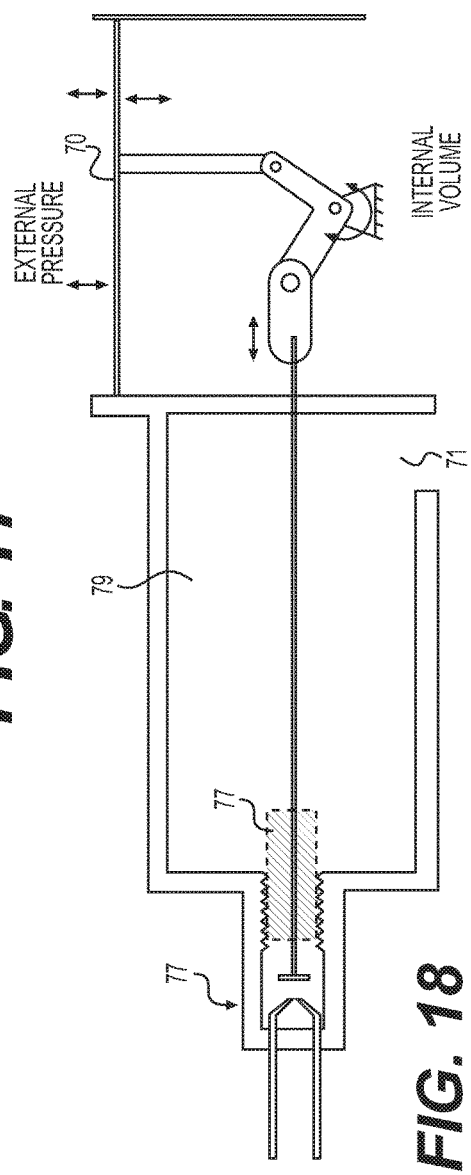
FIG. 18 is an embodiment of a modified secondary regulator.

FIG. 18 shows an embodiment of a modified secondary regulator (demand regulator) with a diaphragm 70 actuated valve 75, a porous plate or diffusion element 77, a settling and muffling cavity 79 and a port 71 for silenced air to enter the breathing mask.

Figure 19:
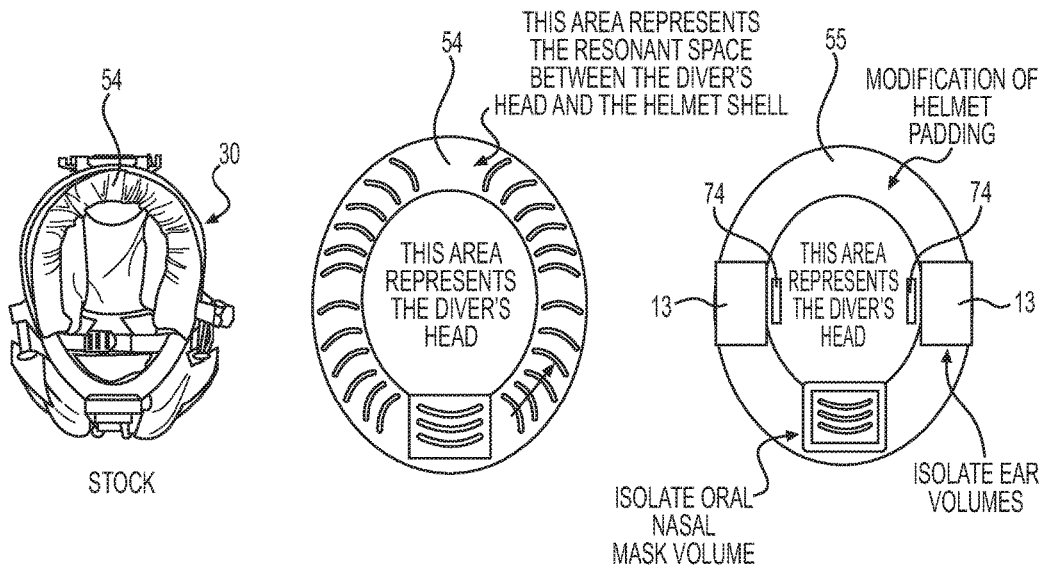
FIG. 19 shows the stock padding inside a dive helmet and a depiction of a modified helmet padding with ear muff cups, separated from the overall padding.

FIG. 19 shows the stock padding 54 inside a dive helmet 30 and a depiction of a modified helmet padding 55 with ear muff cups 13, separated from the overall padding. Changes in padding makeup can improve acoustic damping within the helmet. As supplied, the dive helmet 30 is well padded, although the padding 54 exists primarily for the comfort of the diver. The padding 54 has been modified by creating earmuff cups 13 separated from the overall padding 55, reducing the resonant volume around the ears and isolating them from helmet noise created by the communications system. Earphones 74 are mounted in the earmuffs that are separate from the padding.

Figure 20:
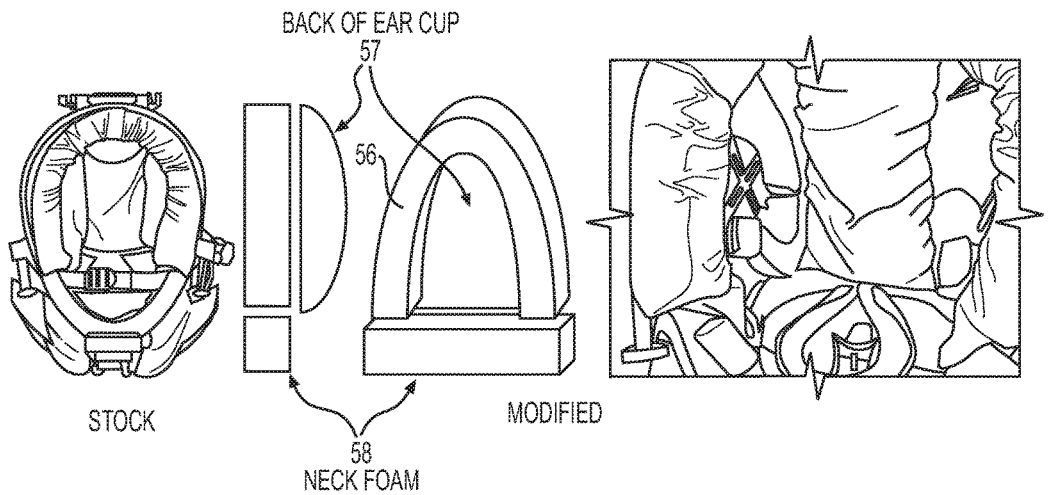
FIG. 20 shows the individual components of the earmuff assembly including backs to the ear cups and neck foam.

FIG. 20 shows an example of an earmuff cup assembly 13 including padding arches 56, backs 57 to the ear cups and neck foam 58. The earmuff 13 can be designed as a slide-in earmuff such that the helmet 30 may be easily put on and taken off without stress to the ears. The lower neck foam section 58 of the new hood cushion 55 helps form the lower boundary of the earmuff 13 as the neck dam assembly 58 is clamped to the helmet 30 from below. The new modified helmet padding separates the earmuff assembly from the overall padding for improving communications.

Figure 21:
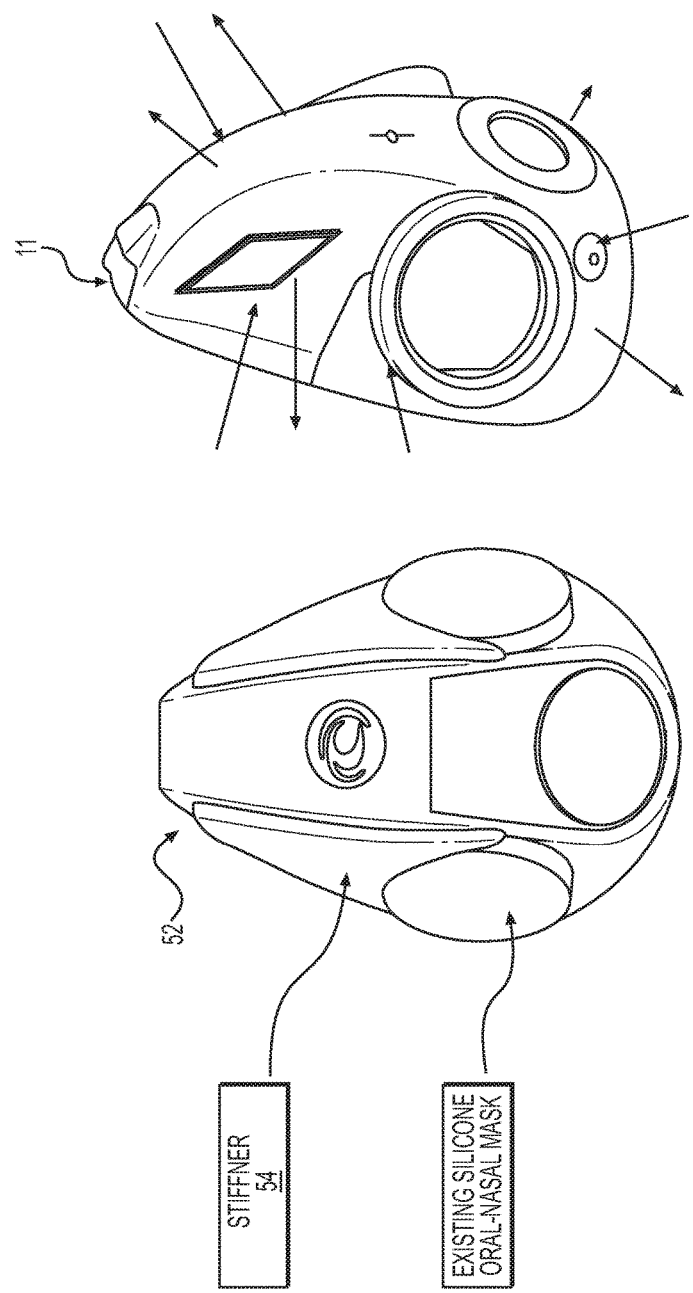
FIG. 21 shows a modified oral-nasal mask implemented to reduce self-communication noise.

FIG. 21 shows an unmodified oral-nasal mask damping jacket 11 on the right. On the left shows the new modified oral-nasal mask 52 improvement implemented to reduce self-communication noise. A dampening jacket 11 that isolates the mask's internal microphone from noise inside the helmet is added to the oral-nasal mask 52. The modified oral-nasal mask 52 with stiffener 54 reduces silicone mask speech vibration noise.

Figure 22:
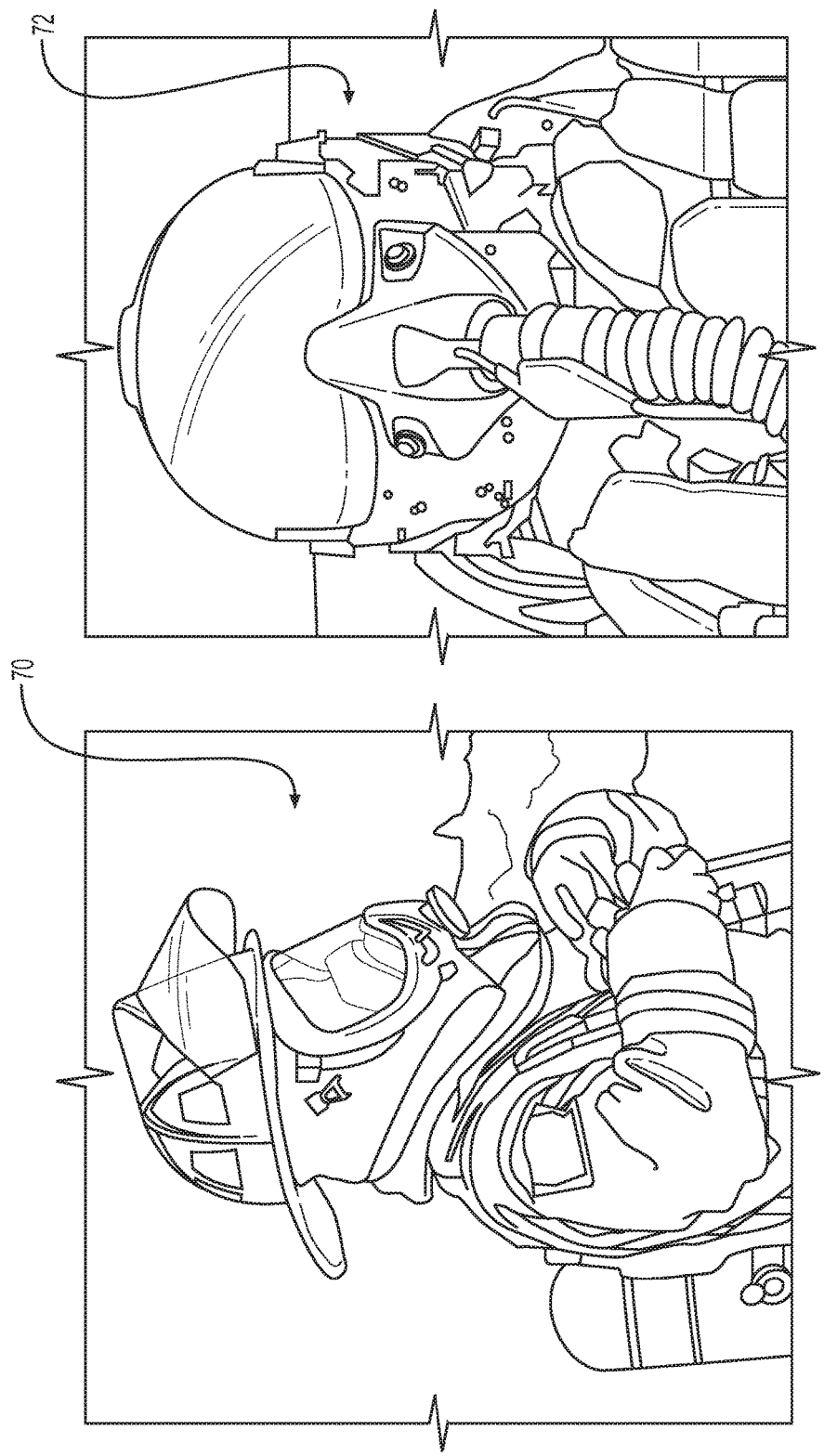
FIG. 22 shows self-contained breathing apparatus (SCBA) used by fire personnel and oxygen masks used by pilots.

FIG. 22 shows self-contained breathing apparatus (SCBA) 70 used by fire personnel and oxygen masks 72 used by pilots. In general, voice communications will be progressively degraded as background noise levels increase. This is a well-documented problem with fire fighters and other first responders that are working in high noise environments and may be wearing a self-contained breathing apparatus. Fighter pilots are prone to this problem as well while wearing oxygen masks. The new quiet demand regulator 40 will eliminate the regulator inhalation noise, thus improving communications on its own and reducing the requirement of the communications system.

While the invention has been described with reference to specific embodiments, modifications and variations of the invention may be constructed without departing from the scope of the invention, which is defined in the following claims.

We claim:

1. Apparatus comprising:
a breathing mask having:
a breathable gas inlet,
a demand regulator connected to the breathable gas inlet,
a silencer connected to the breathable gas inlet,
a first muffling cavity chamber connected to the demand regulator for reducing noises of breathing, air flow and the demand regulator,
further comprising a helmet connected to the breathing mask, padding inside the helmet for contacting a user's head, earmuff assemblies separately mounted in apertures in the padding, and earphones mounted in the earmuffs that are separate from the padding,
wherein the padding further comprises separate padding arches over the earmuffs and separate ear cup backs between the earmuffs and the helmet for isolation of the earmuffs.

2. The apparatus of claim 1, further comprising a sintered filter connected to the first muffling cavity chamber.

3. The apparatus of claim 2, further comprising a second muffling cavity chamber connected to the first muffling cavity chamber and to the breathing mask.

4. The apparatus of claim 3, further comprising a muffler body connected to the breathing mask and enclosing the first muffling cavity chamber and the second muffling cavity chamber.

5. The apparatus of claim 1, wherein the breathing mask is an oral-nasal mask, facial mask, abrasive blasting hood or other breathing device.

6. The apparatus of claim 1, further comprising a view port connected to the breathing mask, an air train supply connected to the view port, a sintered filter connected to the air train supply, a settling shroud connected to the sintered filter, and a curved free flow air train connected to the settling shroud and mounted near a top of the view port for flowing air over the view port.

7. The apparatus of claim 1, further comprising an oral-nasal mask volume sound isolator connected to a lower part and a front of the padding.

8. The apparatus of claim 1, further comprising an oral-nasal mask having an inner dampening jacket for isolating a microphone mounted in the oral-nasal mask from noise inside the helmet.

9. The apparatus of claim 1, wherein the helmet comprises multiple layers of distinct material, thickness, or densities.

10. The apparatus of claim 1, wherein the breathing mask is a fireman's mask, pilot's oxygen mask, abrasive blasting hoods or other breathing devices.

11. Apparatus comprising helmets for wearing on user heads, padding inside the helmets for contacting user heads, voids in the padding for receiving earphone earmuffs, ear cup backs in the voids against the helmet earphone earmuffs for inserting into the voids, neck foam sections forming lower boundaries of the earphone earmuffs, and the helmets configured for slidably positioning over and removing above the earmuffs, wherein the padding further comprises separate padding arches over the earmuffs and separate ear cup backs between the earmuffs and the helmet for isolation of the earmuffs.

12. Method of silencing with a quiet demand-regulated inhalation and mask-clearing device comprising:
providing a breathing mask,
providing a breathable gas inlet on the mask,
providing a demand regulator connected to the breathable gas inlet,
providing a silencer connected to the breathable gas inlet,
providing a first muffling cavity chamber connected to the breathable gas inlet for reducing noises of breathing, air flow and the demand regulator,
providing a sintered filter connected to the first muffling cavity chamber,
a user breathing while wearing the breathing mask,
wherein the breathing mask is a facial mask and further comprising providing an air train supply connected to the facial mask, providing a second sintered filter connected to the air train supply, providing a settling shroud connected to the second sintered filter, and providing a curved free flow air train connected to the settling shroud and mounted near a top of a view port for flowing air over the view port,
further comprising providing a helmet connected to the facial mask, providing padding inside the helmet for contacting a user's head, providing openings in the padding, providing earmuffs separately mounted in the openings, and providing earphones mounted in the earmuffs that are separate from the padding,
wherein the providing the padding further comprises providing separate padding arches over the openings and the earmuffs and providing ear cup backs between the earmuffs and the helmet for sound isolation of the earmuffs.

13. The method of claim 12, further comprising providing a second muffling cavity chamber connected to the first muffling cavity chamber, and providing a body enclosing the first muffling cavity chamber and the second muffling cavity chamber and connecting the body to the breathing mask.

14. The method of claim 12, wherein the breathing mask is an oral-nasal mask.

15. The method of claim 14, further comprising providing an oral-nasal mask volume sound isolator connected to a lower part and a front of the padding and providing an inner dampening jacket between the helmet and the oral-nasal mask for isolating a microphone mounted in the oral-nasal mask from noise inside the helmet.

16. The method of claim 12, wherein the helmet comprises multiple layers of distinct material, thickness or densities.

17. The apparatus of claim 1, wherein the breathing mask is configured for silencing the breathing mask with a quiet demand-regulated inhalation and mask-clearing system.

18. A silenced head gear apparatus with a quiet demand-regulated inhalation and mask-clearing system comprising:

a quiet demand regulator comprising a device for reducing generation of inhalation noise, the device for reducing generation of inhalation noise comprising a porous filter immediately adjacent to a demand valve opening with minimal volume between the demand valve opening and the porous filter such that full pressure behind the demand valve is immediately transferred to a backside of the porous filter, the porous filter through which supply air flows limiting frequencies of generated sound based on hole size and pressure drop, a chamber downstream of the porous filter which fills with air via the porous filter when the demand valve opens, the chamber forming a settling chamber for air from the porous filter for high frequency generated from high pressure air flowing through small orifices of the porous filter.

19. The apparatus of claim 18, further comprising at least one porous or sintered filter connected to a supply pipe at small standoff distance from the viewport with an output of the filter directed toward the viewport.

20. The apparatus of claim 18, further comprising an earmuff assembly for isolating noise inside other parts of the helmet from the user's ears.

21. The apparatus of claim 20, wherein the earmuff assembly comprises separate earcup backs integrated with padding arches for sealing all but a bottom part of the earmuff and a closing pad engaged after a user puts the head gear on to better isolate an earmuff cavity from rest of the helmet.

* * * * *